US00PP35473P2

(12) United States Plant Patent
Hansen

(10) Patent No.: US PP35,473 P2
(45) Date of Patent: Nov. 14, 2023

(54) ***ORIGANUM* PLANT NAMED 'GILT TRIP'**

(50) Latin Name: *Origamum vulgare*
Varietal Denomination: Gilt Trip

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,939

(22) Filed: Jan. 26, 2023

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./258, 263.1
See application file for complete search history.

*Primary Examiner* — Susan McCormick Ewoldt

(57) ABSTRACT

The new and distinct hardy perennial plant, *Origanum* 'Gilt Trip', has dense, rounded, habit with heavily-branched spreading stems. The foliage is ovate, and chartreuse to light-yellow and resists burning when planted in full sun. Flowering begins in early summer and continues to early fall or frost with light lavender petal colors with persistent mauve calyces. The new plant is attractive and useful in the landscape en masse, as an accent, or in containers.

1 Drawing Sheet

Botanical denomination: *Origanum vulgare.*
Variety designation: 'Gilt Trip'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 1, 2022. Subsequently, the new plant was advertised in the "Walters Gardens 22-23 Catalog" by Walters Gardens, Inc. released on Jun. 8, 2022. The claimed plant was first sold to the public on Jul. 25, 2022, by Walters Gardens, Inc., who obtained the plant and all information relating thereto, from the inventor. No plants of *Origanum* 'Gilt Trip' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Origanum* named 'Gilt Trip'. The new plant resulted from a cross of the unreleased, unnamed, proprietary seedling of 'Dr. Ietswaart' (not patented) as the female parent and the unreleased, proprietary hybrid known by 14-6 (not patented) as the male parent on Jun. 30, 2015, at a wholesale perennial nursery in Zeeland, Michigan. Seed was harvested in the summer of 2015 and given the breeder code 15-8-5 during the trial stages of the summer of 2017. The new plant has been asexually propagated initially by division in the fall of 2017 followed by shoot tip cuttings since the summer of 2019 with the resultant plants remaining identical to the original plant, stable and true to type in successive generations.

SUMMARY OF THE INVENTION

*Origanum* 'Gilt Trip' is different from its parents and all other Ornamental Oregano known to the inventor. The nearest comparison cultivars known to the inventor are 'Dr. Ietswaart' (not patented), which is one of the grandparents of the new plant, 'Drops of Jupiter' U.S. Plant Pat. No. 33,676, and 'Aures' (not patented).

'Dr. Ietswaart' has a broader habit and the flowers are very pale lavender to nearly white. 'Drops of Jupiter' has a larger habit with stronger stiffer stems and is more floriferous with darker flowers and bracts. 'Aurea' has a taller habit with flowers that are paler pink with less significant bracts.

The female parent (the seedling of 'Dr. Ietswaart') is taller and looser in habit with darker flowers. The male parent known as 14-6 has a taller habit with darker flowers.

The present invention has not been evaluated under all possible environmental conditions. The phenotype may vary with changes in the environment such as light, temperature, water and nutrient availability, etc. without a change in the genotype of the plant. *Origanum* 'Gilt Trip' is unique from all other Ornamental Oregano known to the inventor in the following combined traits:

1. Habit is a dense, rounded, mound with heavily-branched stems spreading with maturity;
2. Foliage is ovate and chartreuse to light-yellow when planted in full sun and resists burning;
3. Flowers are light lavender with showy and persistent mauve calyces;
4. Flowering begins in early summer and is effective with bracts into early fall or until frost.

BRIEF DESCRIPTION OF THE DRAWINGS

The photographs of the new plant *Origanum* 'Gilt Trip' are in a full sun trial garden in Zeeland, Michigan and demonstrate the unique aspects of the new plant. The colors are as accurate as reasonably possible with color reproductions. Ambient light spectrum, temperature, source, and direction may cause the appearance of minor variations in color.

DETAILED PLANT DESCRIPTION

Figure 1:
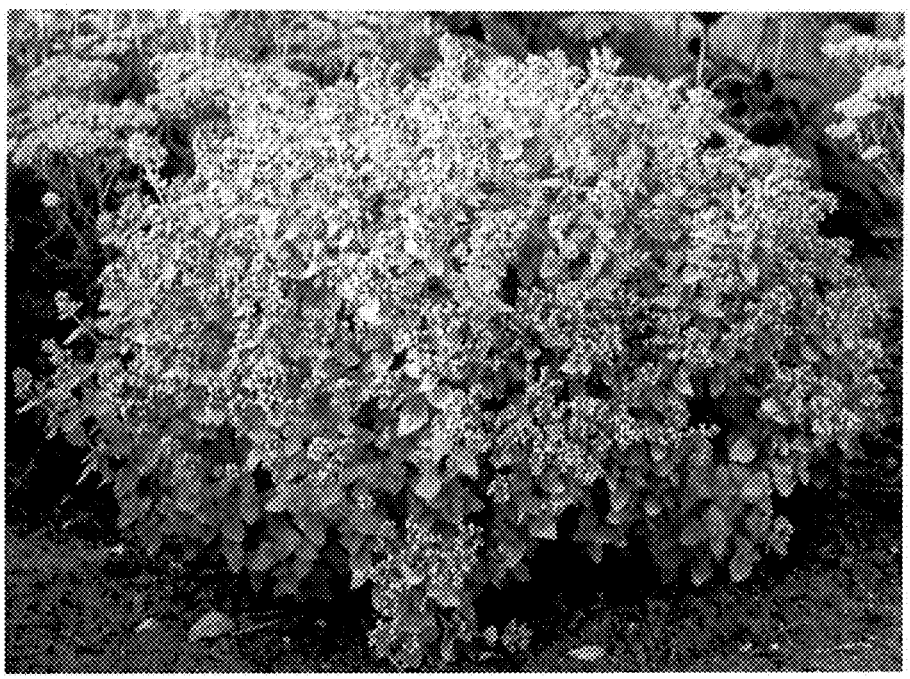
FIG. 1 shows the overall habit of a two-year-old plant in mid-season flowering.
Figure 2:
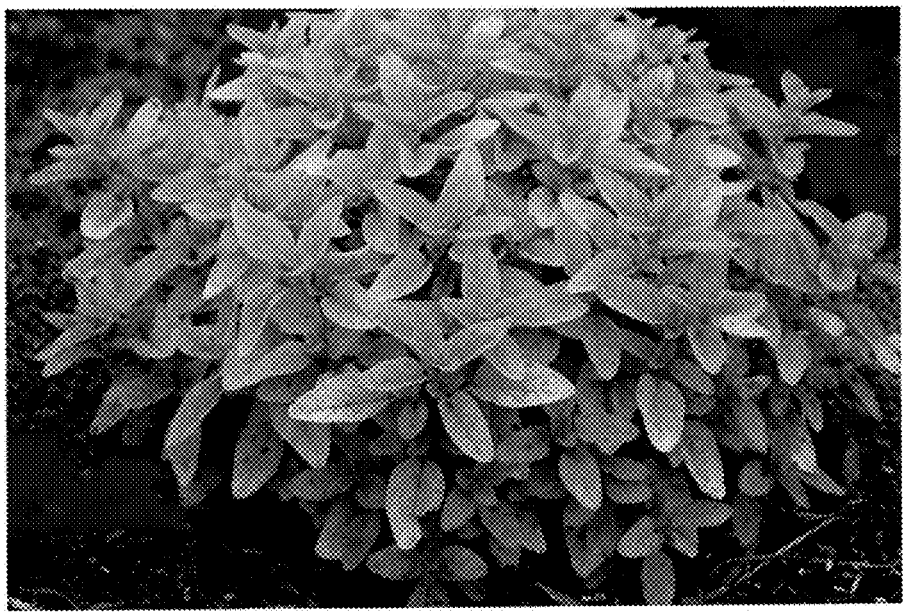
FIG. 2 shows a close-up of the foliage on a one-year-old plant prior to flowering.

The following descriptions are based on a two-year-old plant of *Origanum* 'Gilt Trip' grown in a full-sun display garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture, and maturity levels, but without any change in the genotype.

Parentage: The female or seed parent is the proprietary unnamed seedling of the cultivar 'Dr. Ietswaart', the male or pollen is known only as 14-6;

Plant habit: Herbaceous perennial; fast-growing bushy mound to about 36 cm tall and 75 cm wide at the soil level when in peak flower;

Growth: Rapid; finishing in a standard #1-15 cm container in about 10 to 12 weeks from rooted plug; time to initiate roots at 23° C. about one to two weeks;

Root: Fine, freely branching; color nearest RHS 155D depending on soil type and nutrient content;

Foliage: Opposite; simple; ovate; rounded apex; rounded base; margin entire to micro-ciliolate; puberulent adaxial and abaxial; adaxial and abaxial surface matte;

Leaf blade size: To about 50 mm long and 20 mm wide on lower main stern, decreasing in size distally;

Leaf color: Young adaxial between RHS 144A and RHS N144D, young abaxial between RHS 145A and RHS N145D; mature adaxial variable becoming lighter yellow distally and with more light exposure, comprising RHS 158B, RHS 145A, and between RHS 18A and RHS 11A; mature abaxial variable comprising RHS 146D, RHS 146C, and RHS 158A becoming more and lighter yellow with more light exposure;

Leaf fragrance: Pleasantly spicy; strongly aromatic;

Venation: Pinnate; glabrous; slightly impressed on adaxial surface, costate on abaxial surface;

Vein color: Adaxial surface between RHS 144A and RHS N144A, abaxial surface nearest RHS 146D;

Petiole: Flattened; puberulent adaxial and abaxial;

Petiole size: To about 8 mm long and 2 mm wide at base, decreasing distally;

Petiole color: Both adaxial and abaxial between RHS 146D and RHS 145C;

Stem: About 50 main stems per plant; micro-puberulent; quadrangular, about 4.5 mm across at base and to about 45 cm long; upright to outwardly; heavily compound branching in about the distal 10 nodes; to about 16 branches up to about 20 cm long and about 1 mm across at base, decreasing distally; branch angle about 45 degrees above horizontal; proximally becoming.

Internodes: About 20 per stem; average about 2.3 cm apart with greatest distance in the middle of the stem, decreasing proximally and distally;

Stem color: Variable; young actively growing nearest RHS 145C, older, proximal, semi-woody portion nearest RHS N202A; node color typically same as surrounding stem;

Inflorescence: Compact cyme with small ornamental bracts subtending individual flowers; to about 18 flowers per branchlet; flowering in distal 18 cm to about 22 cm wide;

Flowering season: From about early summer to early fall;

Peduncle: Mostly vertical, puberulent; cylindrical; stiff; strong; to about 2.5 cm long and 0.2 cm diameter; with about 18 flowers;

Peduncle color: Variable; young nearest RHS 145C, older nearest RHS 187D to nearest RHS N186A;

Pedicel: Sessile;

Flower bud: One day prior to opening—obovate; about 4 mm long and 1 mm wide near apex;

Flower bud color: Petal portion between RHS 75D and RHS 69C, calyx portion between RHS 71C and RHS N77B;

Flowers: Zygomorphic; bilabiate; about 8 mm long to exserted pistil, about 3 mm wide, and 3.5 mm tall; sympetalous; bisexual or lacking androecium;

Corolla: About 6 mm long, 3 mm wide, and 3.5 mm tall; fused tube portion about 4 mm long, 2 mm diameter at distal fusion portion, and 1 mm diameter at base; consisting of an upper tri-lobed labium and lower single-lobed labium;

*Upper lip*.—Bi-lobed; each lobe rounded apex and entire margin; to about 1.5 mm long and 5 1 mm wide.

*Upper lip color*.—Adaxial and abaxial between RHS 76C and RHS 84D with base nearest RHS NN155D, no significant color change with maturity.

*Lower lip*.—Tri-lobed; center lobe rounded apex and entire margin, about 1 mm long and 1 mm wide; two side lobes rounded apex and entire margin, about 1 mm long and 0.7 mm wide.

*Lower lip color*.—Adaxial and abaxial between RHS 76C and RHS 84D with base nearest RHS NN155D, no significant color change with maturity.

Calyx: Campanulate; synsepalous, 5-merous fused into calyx tube; 2 mm long and 1 mm across;

Sepals: Five; glabrous; fused in basal 1.5 mm and free in distal 0.5 mm; acute apex, base fused; persistent after flower drop; about 2 mm long and 0.5 mm across at fusion;

Sepal color: Adaxial and abaxial base nearest RHS 145A, adaxial and abaxial apices nearest RHS 146D with blush of nearest RHS 187C;

Bracts: Below each flower and branch; ovate, acute margin, attenuate base, glabrous adaxial and abaxial; to about 5 mm long and 3 mm across near middle;

Bract color: Adaxial and abaxial the same; nearest RHS 145A proximally and distally between RHS 187C and RHS 187D;

Gynoecium: Single; to about 8 mm long;

*Style*.—Cylindrical; glabrous; about 5.5 mm long and 0.3 mm diameter; color in proximal portion nearest RHS 76D, distally posterior to stigma between RHS 76B and RHS 76C.

*Stigma*.—Bifid; about 0.7 mm long; color nearest RHS 76B.

*Ovary*.—Superior; globose; about 0.5 mm diameter; ovary color nearest RHS 145B.

Androecium: Four;

*Anthers*.—Basifixed; globose; about 0.2 mm diameter; color nearest RHS N187B.

*Filaments*.—Adnate inner corolla tube; various lengths from about 1 mm to 5 mm and about 0.1 mm diameter; color nearest RHS NN155D.

*Pollen*.—Not observed.

Flower fragrance: No distinct fragrance was observed from flowers;

Seed: Ellipsoidal; with acute base and rounded apex; to 1 mm long, 0.5 mm across; color variable, nearest RHS 200A to RHS 200D;

Pest and disease: Susceptibility or resistance beyond that which is typical for *Origanum* but typically not prone to browsing by deer or rodents. The new plant has not been found to be susceptible to bacterial or fungal leaf spots. The foliage resists burning in full sun.

Hardiness: Hardy from USDA zones 4 through 9;

I claim:

1. The new and distinct hardy perennial plant, *Origanum* 'Gilt Trip' essentially as herein described and illustrated.

* * * * *